United States Patent [19]

Becker, Jr.

[11] Patent Number: 4,475,709

[45] Date of Patent: Oct. 9, 1984

[54] INTRAVENOUS TUBING CLAMPING DEVICE

[76] Inventor: Karl E. Becker, Jr., 275 S. Pershing Ave., Wichita, Kans. 67218

[21] Appl. No.: 398,897

[22] Filed: Jul. 16, 1982

Related U.S. Application Data

[63] Continuation-in-part of Ser. No. 102,112, Dec. 10, 1979, Pat. No. 4,340,201, and Ser. No. 283,807, Jul. 16, 1981, abandoned, said Ser. No. 102,112, is a continuation-in-part of Ser. No. 893,263, Apr. 5, 1978, abandoned, said Ser. No. 283,807, is a continuation of Ser. No. 101,800, Dec. 10, 1979, abandoned, which is a continuation-in-part of Ser. No. 893,263.

[51] Int. Cl.³ .............................................. F16L 55/14
[52] U.S. Cl. ........................................................ 251/6
[58] Field of Search ....................................... 251/4–10

[56] References Cited

U.S. PATENT DOCUMENTS

| | | | |
|---|---|---|---|
| D. 208,753 | 9/1967 | Curry | D91/3 |
| 1,959,074 | 5/1934 | Bloxsom | 251/6 |
| 2,615,668 | 10/1952 | Ernest | 251/7 |
| 2,902,248 | 9/1959 | Barton et al. | 251/8 |
| 2,935,088 | 5/1960 | Thompson et al. | 251/8 X |
| 2,954,028 | 9/1960 | Smith | 251/8 X |
| 3,029,059 | 4/1962 | Hamilton et al. | 251/9 |
| 3,167,085 | 1/1965 | Redmer | 251/8 X |
| 3,285,563 | 11/1966 | Clarkson | 251/8 |
| 3,332,439 | 7/1967 | Burke | 251/8 X |
| 3,410,517 | 11/1968 | Wall | 251/6 |
| 3,572,407 | 3/1971 | Delorme | 251/7 X |
| 3,584,830 | 6/1971 | Koehn | 251/8 |
| 3,588,034 | 6/1971 | Powell | 251/8 |
| 3,630,481 | 12/1971 | McGay | 251/6 |
| 3,685,787 | 8/1972 | Adelberg | 251/6 |
| 3,802,463 | 4/1974 | Dabney | 251/6 X |
| 3,848,634 | 11/1974 | Noiles | 251/8 X |
| 3,893,468 | 7/1975 | McPhee | 251/6 X |
| 3,900,184 | 8/1975 | Burke et al. | 251/6 |
| 3,960,149 | 6/1976 | Bujan | 251/6 X |
| 3,976,277 | 8/1976 | Basel et al. | 251/7 |
| 4,013,263 | 3/1977 | Adelberg | 251/6 |
| 4,034,773 | 7/1977 | Huggins | 251/9 |
| 4,047,694 | 9/1977 | Adelberg | 251/6 |
| 4,065,093 | 12/1977 | Phillips | 251/6 |

FOREIGN PATENT DOCUMENTS

| | | | |
|---|---|---|---|
| 661174 | 4/1963 | Canada | 251/8 |
| 2220860 | 11/1973 | Fed. Rep. of Germany | 251/6 |
| 2512588 | 9/1975 | Fed. Rep. of Germany | 251/6 |
| 2855572 | 10/1979 | Fed. Rep. of Germany | 251/6 |
| 10829 | 9/1964 | Spain . | |

OTHER PUBLICATIONS

Manufacturer's Literature copyrighted Aug. 1977 by McGaw Laboratories for "Accu Clamp Flow Rate Regulator".

Fonkalsrud et al. "A New Even-Flow Intravenous Infusion Clamp", Arch. Surg., vol. 102, May 1971, pp. 530–531.

Primary Examiner—Martin P. Schwadron
Assistant Examiner—Sheri Novack
Attorney, Agent, or Firm—Fleit, Jacobson, Cohn & Price

[57] ABSTRACT

An intravenous tubing clamping device is provided for controlling fluid flow through compressible tubing. The device includes an elongated member having a proximal end and a distal end which is adapted to receive the tubing. The body member has a generally V-shaped longitudinally extending bottom wall having an angle of about 60° to 165° defining two supporting surfaces for the tubing. In one embodiment, the buttoms of the side walls of the body member define ledges on opposite sides of the V-shaped bottom wall. In another embodiment, the body member defines two grooves on opposite sides of the V-shaped bottom wall. A roller is mounted on the body member for movement longitudinally of the body member. The roller has a generally V-shaped circumference having an apex angle centrally located on the roller having a value of about 60° to 180°. The roller also has circumferentially extending grooves extending around both opposite sides of the outer periphery of the roller. With the clamping device, the lumen or orifice formed in the tubing is generally V-shaped, and the sides of the tubing are clamped to provide a relatively uniform flow rate and to minimize the effects of abusive tugs on the clamped tubing.

23 Claims, 15 Drawing Figures

INTRAVENOUS TUBING CLAMPING DEVICE

CROSS-REFERENCE TO RELATED APPLICATION

This is a continuation-in-part of application Ser. No. 102,112, filed Dec. 10, 1979, now U.S. Pat. No. 4,340,201, which is a continuation-in-part of application Ser. No. 893,263, filed Apr. 5, 1978, now abandoned. This application also is a continuation-in-part of application Ser. No. 283,807, filed July 16, 1981, now abandoned, which is a continuation application of Ser. No. 101,800 filed Dec. 10, 1979, now abandoned, which is a continuation-in-part of Application Ser. No. 893,263.

BACKGROUND OF THE INVENTION

1. Field of the Invention

This invention relates to a clamping device for regulating fluid flow through flexible tubing and, more particularly, to a clamping device for use in intravenous parenteral fluid administration sets.

2. Description of the Prior Art

Many clamps have been developed for controlling the rate of flow of parenteral fluid administered to a patient through the plastic tubing which is used for transporting parenteral fluid from the solution container to the patient. However, these clamps have not proved as reliable and accurate in use as desired, particularly with respect to regulating and maintaining uniform flow rates.

Most clamps are designed to flatten tubing so that the walls of the tubing are more or less parallel producing a long flat oval-shaped lumen. The rate of flow of fluid through tubing compressed in this manner is difficult to control precisely. Moreover, there is considerable strain imposed on the plastic by clamps of this type. Under such strain, most plastics undergo "cold flow" to relieve the strain causing the tubing to flatten still further and collapse inwardly thus decreasing the fluid flow rates. As a result, the nurse or attendant must frequently readjust the clamp to maintain relatively constant fluid flow.

A few clamps have been developed which do not flatten the tube uniformly as shown, for example, in U.S. Pat. No. 3,685,787. This clamp consists of a base having a tapered V-shaped groove into which plastic tubing is progressively compressed by a roller in such a manner that there is essentially no space for the plastic to "cold flow" into since the peripheral surfaces of the tubing are confined.

Another attempt to solve the problem of controlling fluid flow in intravenous tubing is described in U.S. Pat. No. 3,802,463. With this device, opposed walls of the tubing are variably compressed to modify the size of a pair of lumens formed along the outer edges of the compressed tubing. Central portions of the opposite walls are brought together in gradually increasing interior surface contact so that the lumens in the uncompressed outer edges gradually decrease in size until flow of fluid through the tubing ceases.

Another problem associated with most clamps is the so-called "abusive tug" problem. The tubing used in intravenous sets for administering parenteral solutions is typically made of soft polyvinyl chloride. When the tubing is intentionally or accidentally given a strong tug, the tubing stretches. When the abusive tug is released, a large increase in flow rate occurs. An example of a clamp designed to avoid the effects of an abusive tug is U.S. Pat. No. 4,047,694. In this clamp, the side portions of the tubing wall are permitted to migrate into recesses formed between undercut shoulder portions of the roller or wheel and the sides of the clamp housing.

SUMMARY OF THE INVENTION

Accordingly, it is an object of the present invention to provide a clamping device for regulating fluid flow through flexible tubing, particularly soft polyvinyl chloride tubing, which results in a relatively constant flow rate with time and minimizes the increase in flow rate which normally occurs after release of an abusive tug.

In accordance with the present invention, an improved clamping device for controlling fluid flow, such as intravenous fluid flow, is provided. The improved clamping device includes a roller and an elongated body member. The body member is formed of longitudinally extending parallel side walls and a bottom wall. Each of the side walls, in an upper region, is provided with a longitudinally extending slot or groove for supporting axially extending trunnions of the roller. The body member at its proximal end is enlarged to allow positioning of the roller within the body member with the trunnions of the roller guided in the slots or grooves of the side walls. The bottom wall has a generally V-shape with the apex of the V-shaped bottom wall positioned below the side walls. The apex angle of the V-shaped bottom wall is about 60° to 165°.

In one embodiment of applicant's invention, the distal or divergent ends of the V-shaped bottom wall merge with the bottoms of the side walls.

In another embodiment of applicant's invention, the bottoms of the side walls of the body member define body ledges. The body ledges have a substantially constant width and height and extend from the proximal to the distal end of the clamping device. Each of the body ledges is defined by a ledge surface which is substantially parallel to the distal or divergent ends of the V-shaped bottom wall, and a ledge surface which is substantially perpendicular to the axis of rotation of the roller.

In still another embodiment of applicant's invention, the body member defines two body grooves on opposite sides of the V-shaped bottom wall. The body grooves have a substantially constant width and depth and extend longitudinally from the proximal to the distal end of the clamping device. Each of the body grooves defines a body surface which is substantially parallel to the distal or divergent ends of the V-shaped bottom wall, and a body surface which is substantially perpendicular to the axis of rotation of the roller.

The outer circumference of the roller also has a generally V-shape having its apex positioned centrally of the roller and its distal or divergent ends extending toward the axis of rotation of the roller. The apex angle of the roller is selected based on the angle of the apex of the bottom wall and is about 60° to 180°. Preferably, the apex angle of the roller is 10° to 50° more than the apex angle of the V-shaped bottom wall. The roller also has circumferentially extending roller grooves extending around both opposite sides of an outer circumferential portion or the outer periphery of the roller.

In one embodiment of the roller, the grooves have a substantially constant width and depth. Each of such roller grooves defines a roller surface which is substantially parallel to the axis of rotation of the roller, and a roller surface which is substantially perpendicular to the axis of rotation of the roller. These surfaces cooperate with side walls of the body member to clamp sides of the tubing so that substantially all fluid flow is through a central portion of the tubing.

In another embodiment of the roller, generally V-shaped grooves are formed on opposite sides of the outer peripheral portion of the roller. The apices of the grooves are inwardly spaced from the side edges of the outer peripheral portion. As a result, the width of the roller decreases in a direction extending from the outer circumference or peripheral portion of the roller towards the axis of rotation of the roller. The portions of the roller defining or forming the grooves cooperate with side walls of the body member to clamp sides of the tubing. The clamping forces on the tubing sides are greatest in the vicinity of the side edges of the outer peripheral portion and decrease towards the axis of rotation of the roller. Preferably, the clamping forces are such that substantially all of the fluid flows through a lumen formed in a central portion of the tubing.

The apex angle of the bottom wall, the apex angle of the roller, and the position or orientation of the supports for the roller provided by the side walls of the body member are interrelated in such manner that longitudinal movement of the roller toward the distal end of the body member progressively compresses flexible tubing positioned between the body member and the roller.

In one embodiment of applicant's invention, the apex angle of the bottom wall is constant while the distance between the supports for the roller and the bottom wall progressively decreases in a direction toward the distal end of the body member. Thus, as the roller moves toward the distal end, the apex of the circumference of the roller progressively moves toward the apex of the bottom wall. In this manner, the lumen or fluid flow passage within the flexible tubing can be progressively reduced until a desired flow rate is obtained or until the tubing is sufficiently compressed to prevent fluid flow.

In another embodiment of applicant's invention, the distance between the supports for the roller and the distal or divergent ends of the V of the V-shaped bottom wall is constant while the apex angle of the bottom wall is progressively changed from a value less than the apex angle of the roller to a value approximately equal to the apex angle of the roller. This progressive change in apex angle is obtained by moving the apex of the bottom wall in an upward direction toward the roller, the width of the V-shaped bottom wall remaining constant.

In still another embodiment of applicant's invention, both the distance between the supports for the roller and the bottom wall and the size of the apex angle of the bottom wall are progressively changed. Thus, this embodiment of applicant's invention combines the features of the two previously discussed embodiments.

With applicant's invention, the lumen or orifice formed in the tubing is generally V-shaped. Thus, compressive forces in the area of the lumen or orifice tend to be generally distributed across this portion of the tubing. This distribution of compressive forces tends to eliminate "cold flow" in the compressed tubing. In addition, since the tubing in the area of the lumen or orifice is clamped in a V-shape, any inward movement of the upper and lower surfaces of the tubing is resisted. Thus, use of the device provides relatively uniform fluid flow through the tubing over extended periods of time. In addition, the size of the lumen or orifice experiences relatively less change during an abusive tug and recovers its size and shape more quickly after the abusive tug is released.

The invention, and its objects and advantages, will become more apparent in the detailed description of the preferred embodiments presented below.

BRIEF DESCRIPTION OF THE DRAWINGS

In the detailed description of the preferred embodiments of the invention presented below, reference is made to the accompanying drawings, in which.

DESCRIPTION OF THE PREFERRED EMBODIMENTS

Figure 1:
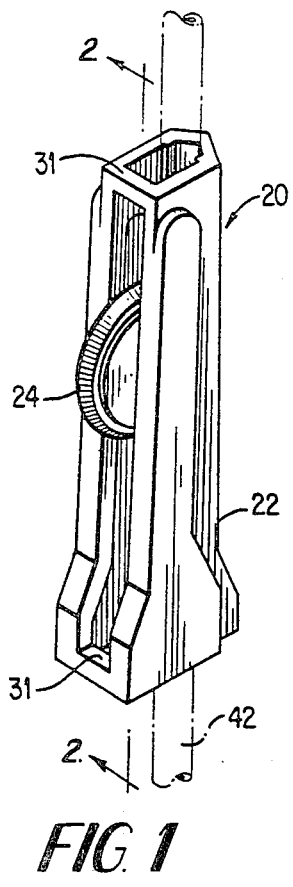
FIG. 1 is a perspective view of one embodiment of a clamping device in accordance with the present invention.
Figure 4:
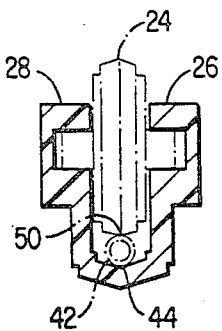
FIG. 4 is a cross-sectional view of the embodiment of FIG. 1 taken along line 4—4 in FIG. 2.

Because clamping devices are well known, the present description will be directed in particular to elements forming part of, or cooperating more directly with, the present invention. Elements not specifically shown or described herein are understood to be selectable from those known in the art.

Referring now to the drawings, and to FIGS. 1-6 in particular, one embodiment of the present invention is illustrated and will be described in connection with a clamping device, generally designated 20.

The clamping device 20 has a body member 22 and a roller 24 operatively associated therewith. The body member 22 and the roller 24 are preferably made of relatively rigid plastic or similar material. The body member 22 is generally elongated and has substantially parallel side walls 26, 28 and a bottom wall or floor 30. One or more members or struts 31 interconnect ends of upper portions of walls 26 and 28.

Figure 2:
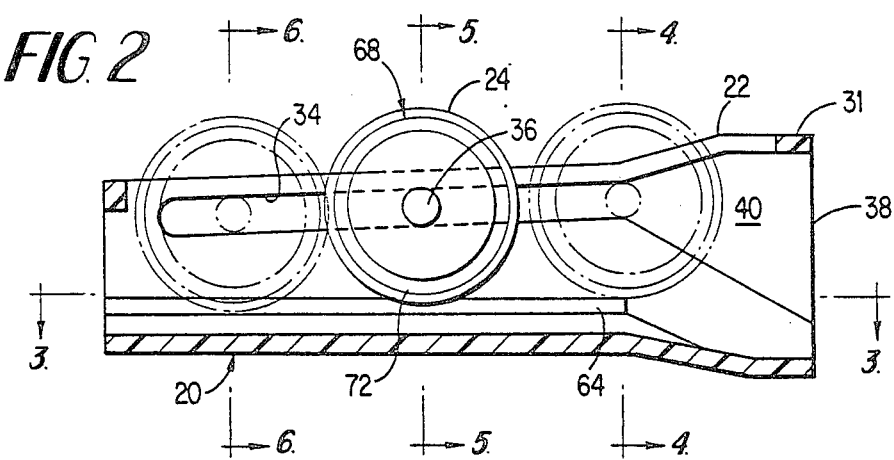
FIG. 2 is a cross-sectional view of the embodiment of FIG. 1 taken along line 2—2 of FIG. 1.

The side walls 26, 28 have grooves or slots 32, 34, respectively, for supporting trunnions 36 which extend axially from the roller 24 to define an axis of rotation extending transversely of the body member 22. As illustrated in FIG. 2, both the proximal end 38 of the body member 22 and slots 32, 34 are enlarged to define an opening 40 which facilitates insertion of roller 24 into the body member. Further, the flared ends of the side walls 26, 28 of the embodiment illustrated in FIG. 2 are axially extended to define a space in which roller 24 can rest without applying pressure to compressible, elongated flexible tubing 42 positioned between the roller 24 and body 22. This feature of applicant's invention greatly facilitates movement of clamping device 20 along tubing 42.

Figure 3:
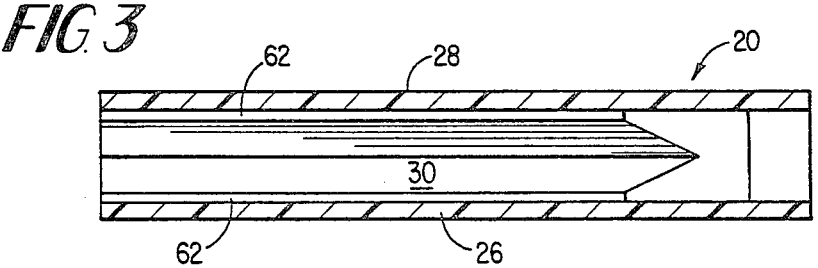
FIG. 3 is a cross-sectional view of the embodiment of FIG. 1 taken along line 3—3 in FIG. 2.

As illustrated in FIGS. 4, 5, 5A and 6, both a supporting portion of bottom wall 30 and the circumference of roller 24 have a generally V-shape. As seen in FIGS. 2 and 3, the supporting portion of bottom wall 30 starts in the vicinity of line 4—4. Also, the roller 24 is positioned in the slots 32, 34 in such manner that the apex 44 of body member 22 and the apex 50 of the roller 24 are in general alignment. Thus, the apices form cooperating clamping members that determine the size of a lumen 56 formed in a central region of tubing 42.

The apex angle of the support or bottom wall 30 can vary from about 60° to 165°, and the apex angle of the wheel or roller 24 can vary from about 60° to 180°. Preferably, the apex angle of the bottom wall is about 105° to 155°, more preferably about 120° to 135°. Also, the apex angle of the roller is preferably about 120° to 170°, more preferably about 150° to 165°. Further, the apex angles of the two members can be either the same or different from each other. Preferably, the apex angle of the wheel or roller should be larger than the apex angle of the support or bottom wall. Normally, it is preferred that the apex angle of the wheel or roller be about 10° to 50° greater than the apex angle of the support, with about 15° to 30° being more preferred.

Figure 5:
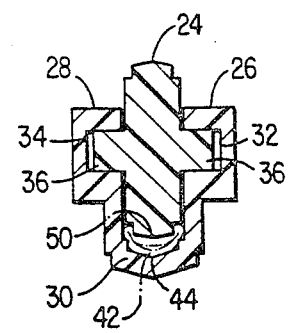
FIG. 5 is a cross-sectional view of the embodiment of FIG. 1 taken along line 5—5 of FIG. 2.
Figure 6:
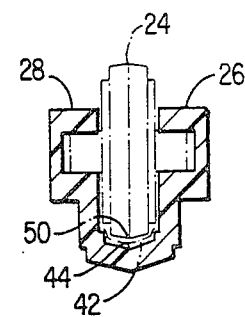
FIG. 6 is a cross-sectional view of the embodiment of FIG. 1 taken along line 6—6 of FIG. 2.
Figure 5A:
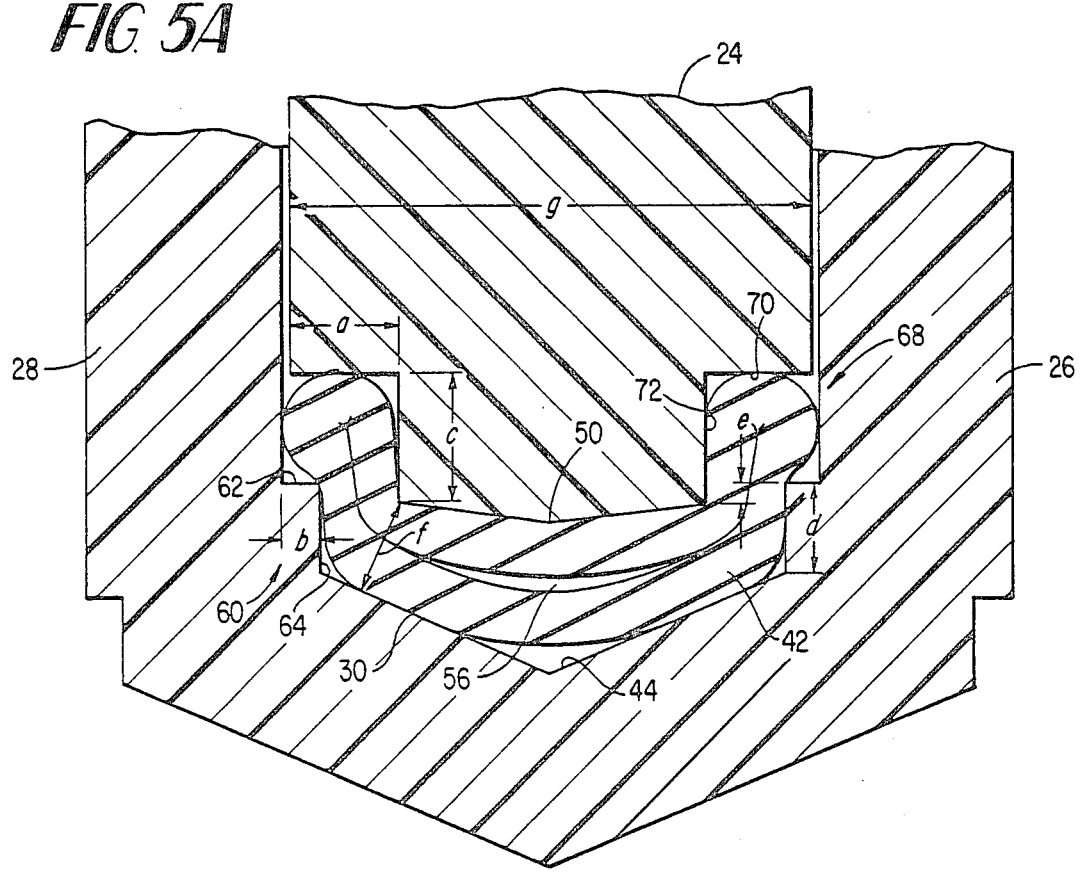
FIG. 5A is an exploded view of the clamping area portion of FIG. 5.

As illustrated particularly in FIGS. 2, 3 and 5A, the bottoms of the side walls 26, 28 form body ledges 60. The body ledges have a substantially constant width and height and extend longitudinally from the proximal to the distal end of the clamping device. Each of the body ledges 60 is defined by a ledge surface 62 which is substantially parallel to the distal or divergent ends and to the apex 44 of bottom wall 30, and a body surface 64 which is substantially perpendicular to the axis of trunnions 36 and substantially parallel to side walls 26, 28. The roller 24 has circumferentially extending roller grooves 68 extending around both opposite sides of the outer periphery of the roller. Each of roller grooves 68 defines a roller surface 70 which is substantially parallel to the axis of trunnions 36 or, in other words, the axis of rotation of roller 24, and a roller surface 72 which is substantially perpendicular to the axis of trunnions 36.

Referring now particularly to FIG. 5A, each of roller grooves 68 has a width "a" which is less than about 2 times the uncompressed nominal wall thickness of tubing 42. Preferably, the width "a" is about 1.6 to 1.8 times the uncompressed nominal wall thickness of tubing 42. With this arrangement, the sides of tubing 42 are under some compression so that no flow lumen is present in the vicinity of roller grooves 68 when the tubing is clamped. This compression is along a line which is substantially parallel to the axis of trunnions 36.

The distance between roller surfaces 70 and ledge surfaces 62 varies in the embodiment illustrated in FIGS. 1-6 depending upon the position of roller 24 relative to the distal end of body member 22. This distance is preferably more than about 2 times the uncompressed nominal wall thickness of tubing 42 when the tubing is being clamped to provide normal flow rates, generally about 80 to 150 ml/hr and, more typically, about 100 to 125 ml/hr. This distance is selected in order to avoid any significant compression of the sides of tubing 42 between roller surfaces 70 and ledge surfaces 62. In other words, this distance is selected to avoid any significant compression of the sides of tubing 42 in a direction which is substantially perpendicular to the axis of trunnions 36.

The most significant compression of the tubing 42 occurs between roller surfaces 72 and ledge surfaces 64. This compression is achieved by controlling the size of the openings between roller surfaces 72 and ledge surfaces 64. More specifically, the width "a" of roller grooves 68 less the width "b" of body ledges 60 should be about 0.9 to 1.3 times, preferably about 1 to 1.2 times, the uncompressed nominal wall thickness of tubing 42. In order to provide adequate compression in this area, a slight overlap "e" is preferably provided at normal flow rates between the plane of ledge surfaces 62 and a line parallel to the axis of trunnions 36 drawn through the distal ends of roller surfaces 72. This overlap is preferably between about 0 to 0.5 times, preferably about 0.25 times, the uncompressed nominal wall thickness of tubing 42. Also, it is generally preferred that the distance "f" between the distal or divergent ends of the V of V-shaped roller 24 and the adjacent V-shaped bottom wall 30 at normal flow rates is about 1.2 to 1.8 times the uncompressed nominal wall thickness of tubing 42. This distance is measured along a line substantially perpendicular to the V-shaped bottom wall 30.

In order to provide the compressions discussed above in the various areas of the tubing 42, it is preferred that the height "d" of ledges 60 is about 1 to 2 times, preferably about 1.5 times, the uncompressed nominal wall thickness of tubing 42. Also, the depth "c" of roller grooves 68 is preferably greater than the height "d" of ledges 60 by about 0.75 to 1.25 times the uncompressed nominal wall thickness of tubing 42. In addition, it is generally preferred that the periphery of the clamping area at normal flow rates be greater than the circumference of the uncompressed tubing 42. The "periphery of the clamping area" is defined to mean the actual periphery around the cross-sectional area defined between body 22 and roller 24 at normal flow rates such as illustrated in FIGS. 5 and 5A.

In operation, tubing 42 is placed inside body member 22 of clamping device 20 and the body member is moved to a desired position on the tubing. Roller 24 is then inserted into the opening 40 and trunnions 36 are positioned in slots 32 and 34. The trunnions and slots are so designed that the trunnions fit in a loose manner within the slots. The gradual slope of the slots 32, 34 provides the ability to constantly control or vary fluid flow rates.

As the roller 24 moves to the left in FIG. 2, apex 50 progressively pinches tubing 42 thus reducing the size of lumen 56 inside tubing 42. Thus, movement of roller 24 provides selective control of fluid flow through tubing 42. It should be noted that the manner in which apex 50 compresses the walls of tubing 42 forms a V-shaped lumen 56, as illustrated in FIGS. 5 and 5A, which tends to evenly distribute the compressive force exerted on tubing 42, thereby reducing the tendency of "cold flow" in the compressed tubing. Moreover, the lumen 56 does not have a tendency to change in size or shape since any movement of the upper or lower wall is balanced by an equal movement of the other wall. In addition, because of the relatively high compressive force exerted on tubing 42 between ledge surfaces 64 and roller surfaces 72, the size of flow lumen 56 undergoes less change during an abusive tug and recovers its size and shape more quickly after the abusive tug is released.

To better illustrate this embodiment of applicant's invention, the dimensions of a preferred clamping device will be described. These dimensions are based on a tubing 42 having an outer diameter of about 0.138 inch, an inner diameter of about 0.100 inch and a nominal wall thickness of about 0.019 inch. The width "a" of roller grooves 68 is about 0.034 inch, the width "b" of body ledges 60 is about 0.012 inch, the depth "c" of roller grooves 68 is about 0.040 inch, the height "d" of body ledges 60 is about 0.027 inch, the overlap "e" is about 0.004–0.005 inch at normal flow rates, the distance "f" is about 0.032 inch at normal flow rates, and the width "g" of roller 24 is about 0.168 inch. With these dimensions, the preferred apex angle of roller 24 is about 165°, and the preferred apex angle of bottom wall 30 is about 135°.

Figure 7:
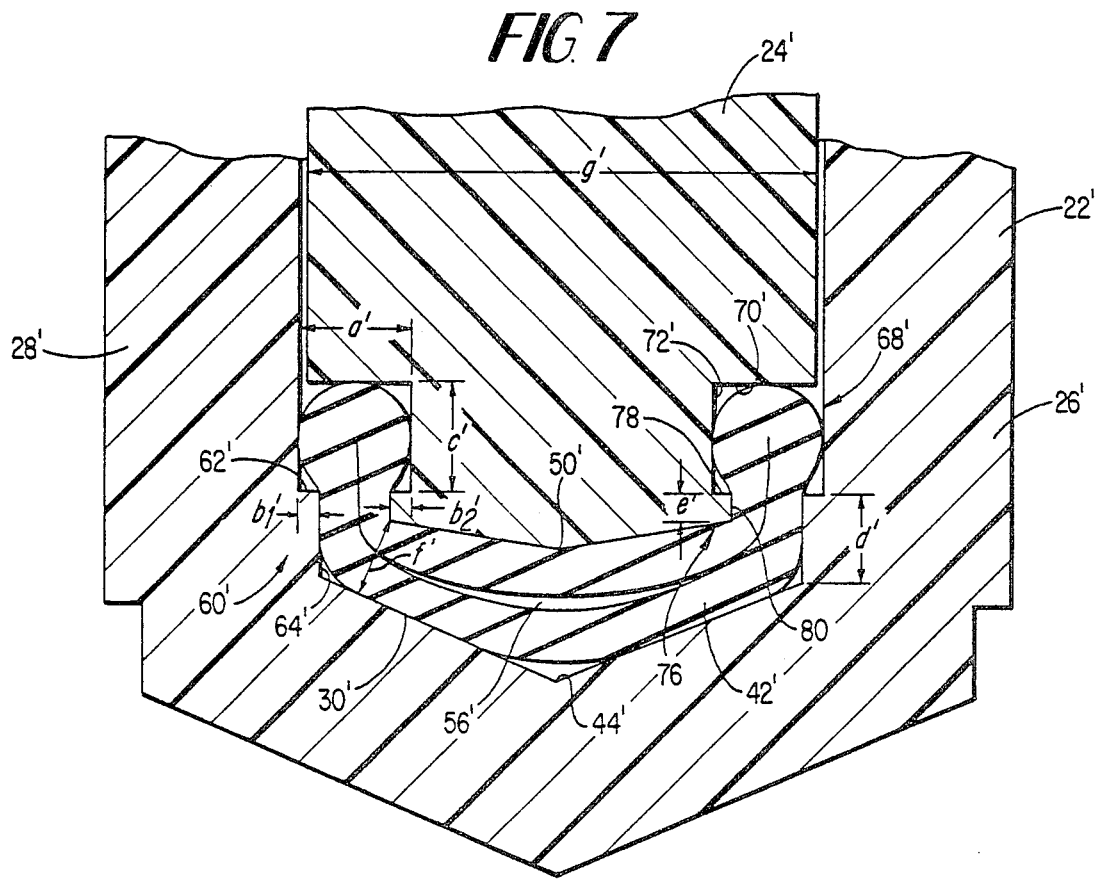
FIG. 7 is a view similar to FIG. 5A of another embodiment of the clamping device of the present invention.

Turning now to FIG. 7, an embodiment of applicant's invention is illustrated which is essentially the same as the embodiment illustrated in FIGS. 1-6 with the exception of the grooves in the roller. With this embodiment, reference numerals with primes attached have been used to identify components similar to components illustrated in FIGS. 1-6.

As illustrated in FIG. 7, roller grooves 68' are formed in roller 24' to define roller ledges 76 at the distal or divergent ends of the V of V-shaped roller 24'. Each of ledges 76 defines a surface 78 which is substantially parallel to the axis of trunnions 36 and a surface 80 which is substantially perpendicular to the axis of trunnions 36. Surfaces 80 of roller ledges 76 face surfaces 64' of body ledges 60'. In this embodiment, the width $b_1'$ of each of body ledges 60' is reduced so that the combined width $b_1'$ of body ledges 60' and the width $b_2'$ of roller ledges 76 ($b_1'+b_2'$) in FIG. 7 is approximately equal to the width "b" of each of body ledges 60 in FIG. 5A. Dimensions a', c', d', e', f' and g' are substantially the same as the corresponding dimensions in FIG. 5A. The clamping device in FIG. 7 operates in essentially the same manner as the embodiment illustrated in FIGS. 1-6 and produces essentially the same compressive forces as discussed with respect to FIG. 5A.

Figure 8:
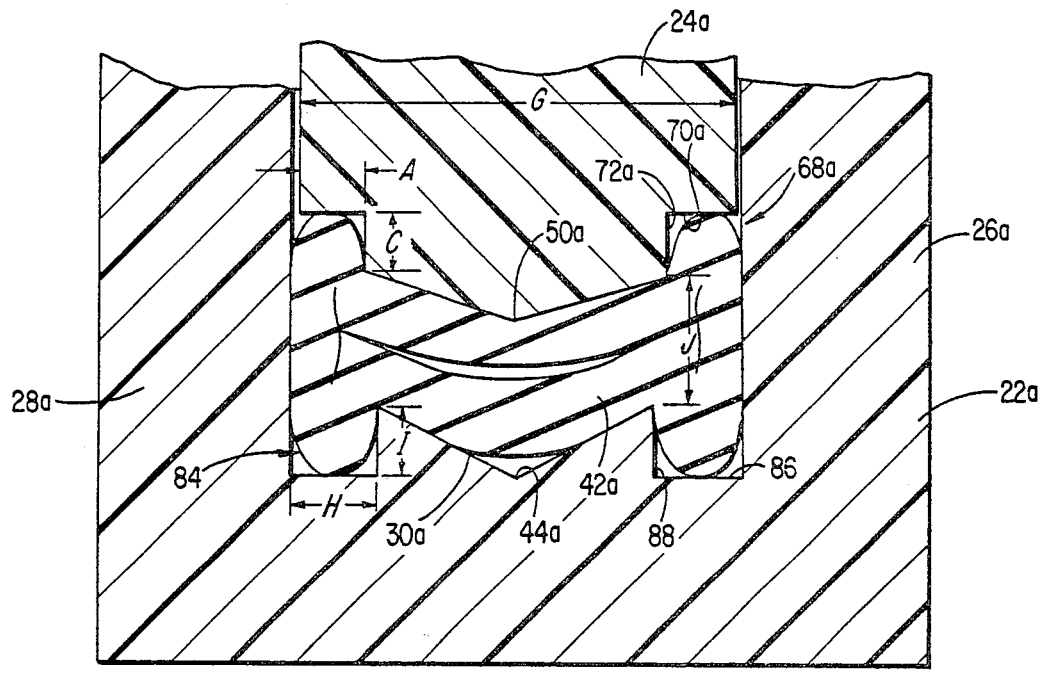
FIG. 8 is a view similar to FIGS. 5A and 7 of still another embodiment of the clamping device of the present invention.

Referring now to FIG. 8, an embodiment of applicant's invention is illustrated in which grooves are formed both in the roller and the body to minimize the effects of an abusive tug. With this embodiment, reference numerals will be combined with alphabetical characters to identify features similar to those previously described with reference to FIGS. 1-6.

In FIG. 8, body member 22a defines two body grooves 84 on opposite sides of V-shaped bottom wall 30a. The body grooves 84 are of constant depth and width and extend longitudinally from the proximal to the distal end of the clamping device. Each of body grooves 84 defines a body surface 86 which is substantially parallel to the distal or divergent ends and to the apex 44a of bottom wall 30a, and a body surface 88 which is substantially perpendicular to the axis of trunnions 36. In this embodiment, the width A of roller grooves 68a is less than about 2 times the uncompressed nominal wall thickness of tubing 42a to provide compression of tubing 42a in the vicinity of roller grooves 68a when the tubing is clamped. This compression is in a direction substantially parallel to the axis of trunnions 36. Preferably, the width A is about 1.2 to 1.5 times the uncompressed nominal wall thickness of the tubing 42a. The width H of body grooves 84, as illustrated in FIG. 8, is slightly greater than the width A of roller grooves 68a. This width H also is less than about 2 times the uncompressed nominal wall thickness of tubing 42a and can be the same or different from the width A. The depth C of roller grooves 68a and the depth I of body grooves 84 are approximately the same and are preferably approximately equal to the uncompressed nominal wall thickness of tubing 42a. The spacing J between the distal or divergent ends of the V of V-shaped roller 24a and the distal or divergent ends of the V of V-shaped bottom wall 30a is about 1.6 to 2.2 times, preferably about 1.8 times, the uncompressed nominal wall thickness of tubing 42a at normal flow rates.

The operation of the clamping device of FIG. 8 is essentially the same as that previously described with reference to FIGS. 1-6. Also in similar manner to the embodiment illustrated in FIGS. 1-6, the compression of the tubing at both sides in a direction substantially parallel to the axis of the roller trunnions (not shown) acts to minimize the increase in flow rate which normally occurs after release of an abusive tug. Also, as with respect to the embodiment illustrated in FIGS. 1-6, no flow lumen is formed at the sides of the tubing 42a when the tubing is clamped.

To better illustrate this embodiment of applicant's invention, the dimensions of a preferred clamping device will be described. These dimensions are based on a tubing having the same dimensions discussed with respect to FIGS. 1-6. The width A of roller grooves 68a is about 0.025 inch, the depth C of roller grooves 68a is about 0.020 inch, the width G of roller 24a is about 0.144 inch, the width H of body grooves 84 is about 0.029 inch, the depth I of body grooves is about 0.021 inch and the spacing J is about 0.038 inch at normal flow rates. With these dimensions, the preferred apex angle of roller 24a is about 150° and the preferred apex angle of bottom wall 30a is about 125°.

Turning now to FIGS. 9-12, an embodiment of applicant's invention is illustrated which is similar to the embodiment illustrated in FIG. 8 except that the clamping area for regulating the flow rate is controlled by increasing the apex angle of the support or body wall from the proximal to the distal end of the clamping device. With this embodiment, corresponding reference numerals in the "100" series have been used to identify components similar to components previously described.

Figure 9:
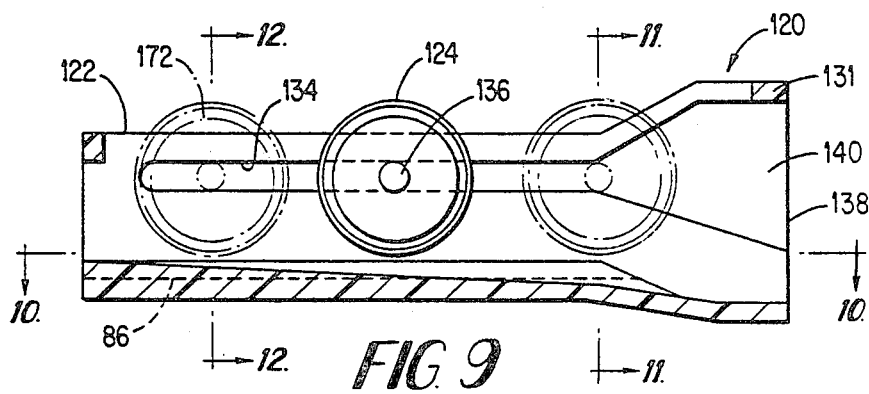
FIG. 9 is a view similar to FIG. 2 of another embodiment of the clamping device of the present invention.
Figure 10:
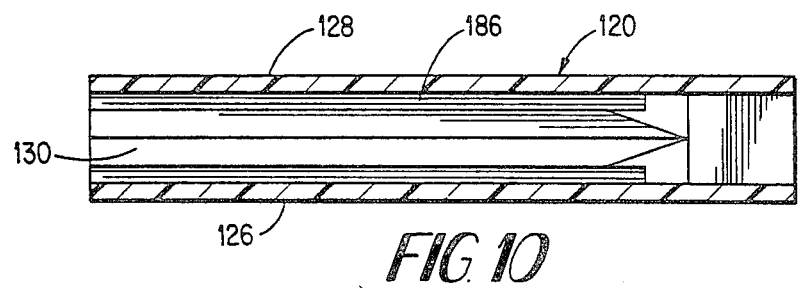
FIG. 10 is a cross-sectional view of the embodiment of FIG. 9 taken along line 10—10 of FIG. 9.

As illustrated in FIGS. 9-12, clamping device 120 has a body 122 formed of substantially parallel side walls 126, 128 and a bottom wall or floor 130. The bottom wall 130 has a generally V-shape with the apex of the V preferably centered between and located below the bottom of the side walls. The side walls 126, 128 include slots or grooves 132, 134 for supporting trunnions 136 of roller 124. As illustrated in FIG. 9, the slots have an enlarged opening 140 and extend longitudinally toward the distal end of body 122. For most of their length, the slots are substantially parallel to the bottom edge of side walls 126, 128.

Figure 11:
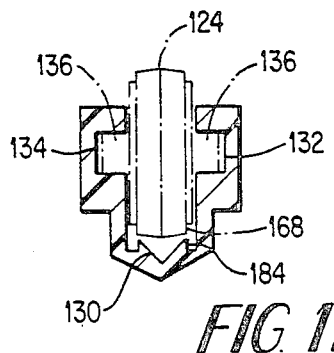
FIG. 11 is a cross-sectional view of the embodiment of FIG. 9 taken along line 11—11 of FIG. 9.
Figure 12:
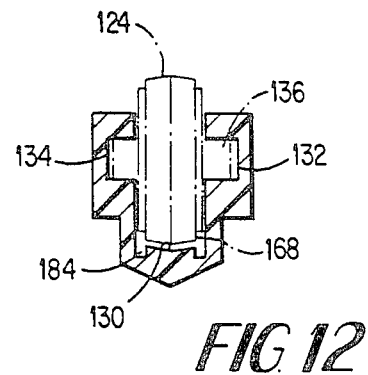
FIG. 12 is a cross-sectional view of the embodiment of FIG. 9 taken along line 12—12 of FIG. 9.

With this embodiment, compression of the tubing 142 for regulating the flow rate is obtained by gradually changing the apex angle of the bottom wall 130. For instance, as illustrated in FIG. 11, the roller 124 has an apex angle of approximately 150° while the bottom wall 130 has an apex angle of approximately 100°. The apex angle of the bottom wall is gradually changed by moving the apex in an upward direction toward the roller until the apex angle of the bottom wall reaches a desired value, such as approximately 150°, as illustrated in FIG. 12. The distance separating the distal or divergent ends of the V-shaped bottom wall 130 or, in other words, the width of the V-shaped bottom wall adjacent body grooves 184, remains unchanged during the upward movement of the apex 144 of bottom wall 130 toward the roller. The embodiment illustrated in FIGS. 9-12 functions in basically the same manner as the embodiment described in FIG. 8 except that the distance J remains constant.

Figure 13:
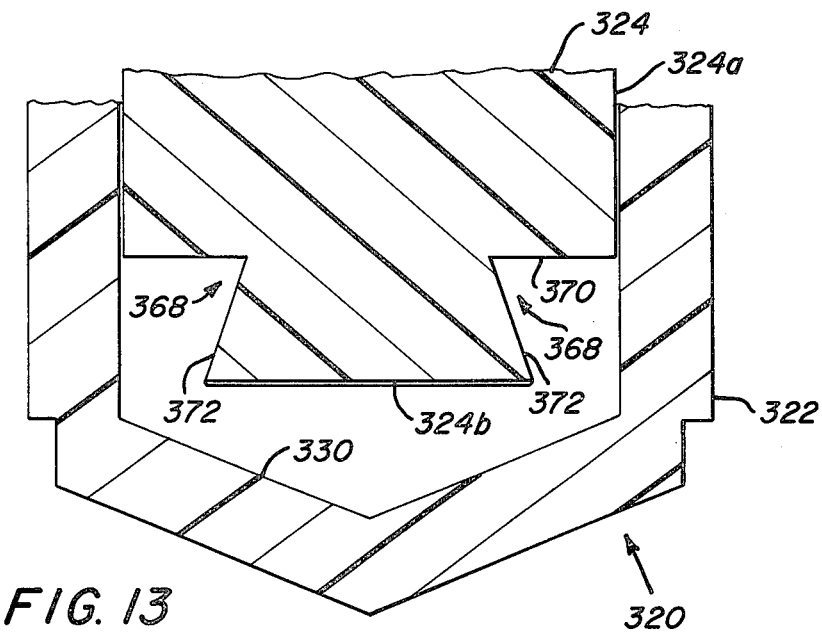
FIG. 13 is a view similar to FIG. 5A of another embodiment of the present invention.

Considering now FIG. 13, still another embodiment of applicant's invention is illustrated. This embodiment is similar to the embodiments illustrated in FIGS. 1 to 8, with the primary difference being the shape of the roller grooves. In the following description, corresponding reference numerals in the "300" series will be used to identify components similar to those previously described.

FIG. 13 illustrates a portion of a clamping device 320 having a body member 322 and a roller 324. The floor 330 of the body member 322 is formed from two planar surfaces having outer edges merging with the bottom edges of the side walls of the body member. Such floor has a V-shaped groove with an apex angle between 60° and 165° for receiving and supporting tubing being compressed. Preferably, the apex angle of the groove is between approximately 120° and 160°, with a value of between approximately 130° and 145° being more preferred.

Preferably, the width and depth of the floor 330 are constant. Compression of the tubing is effected by shaping the side walls of the body member 322 so that the trunnions (not illustrated) of the roller 324 are moved towards the floor 330 as the roller moves from the proximal towards the distal end of the body member. For instance, the supports for the trunnions are shaped to provide a slope of about one degree.

The roller 324 has a central portion 324a carrying the trunnions that has a substantially constant width. An outer peripheral portion 324b of the roller has a width less than that of the central portion and is shaped to cooperate with the floor 330 to clamp a central portion of the tubing so as to define a flow lumen within the tubing. Circumferentially extending roller grooves 368 extend around both sides of the outer peripheral portion 324b of the roller. The grooves are generally V-shaped and have apices inwardly spaced from side edges of the outer peripheral portion. Each of the roller grooves 368 defines a first roller surface 372 extending inwardly toward the center of the roller and a second roller surface 370 interconnecting an inner end of the roller surface 372 with an outer edge of the central portion 324a. The surfaces 372 are tapered inwardly so that the width of the roller progressively decreases in a direction extending inwardly from the outer peripheral portion 324b of the roller.

As with the embodiment illustrated in FIG. 13, the outer peripheral portion 324b of the roller is substantially flat. The roller 324 has a knurled surface to enhance frictional engagement between the roller and the tubing and to facilitate movement of the roller by a user of the clamping device.

In one embodiment of the clamping device illustrated in FIG. 13 that is used to compress tubing having the previously described dimensions, the roller surfaces 372 are planar surfaces extending inwardly from outer sides of the peripheral surface 324b. Extensions of such surfaces form acute angles with the axis of the roller trunnions. Such angles are preferably between 65° and 75°, with values between approximately 69.5° and 70° being especially preferred. The distance between the inner surfaces of the side walls of the body member 322 is preferably between 0.165 and 0.170 inches. The width of the peripheral portion 324b is preferably between approximately 0.104 and 0.122 inches. The width of the peripheral portion 324b and the amount of inward taper of the surface 372 are selected such that no flow lumens are formed in side portions of the tubing. Preferably, the distance between the side or edge of the peripheral portion 324b and the adjacent side surface of the body member 322 is between approximately 1 and 1.7 times the nominal wall thickness of the uncompressed tubing. Preferably, the distance between the outer edge of the peripheral portion 324b and the surface 370 is between 0.030 and 0.045 inches. It is preferable that such vertical distance be such that outer ends of the tubing side portions just contact the surfaces 370 during regulation of normal flow rates so that minimal compressive forces acting in directions perpendicular to the axis of the trunnions are exerted on portions of the tubing received in the spaces defined between the grooves 368 and the body member side walls.

Figure 14:
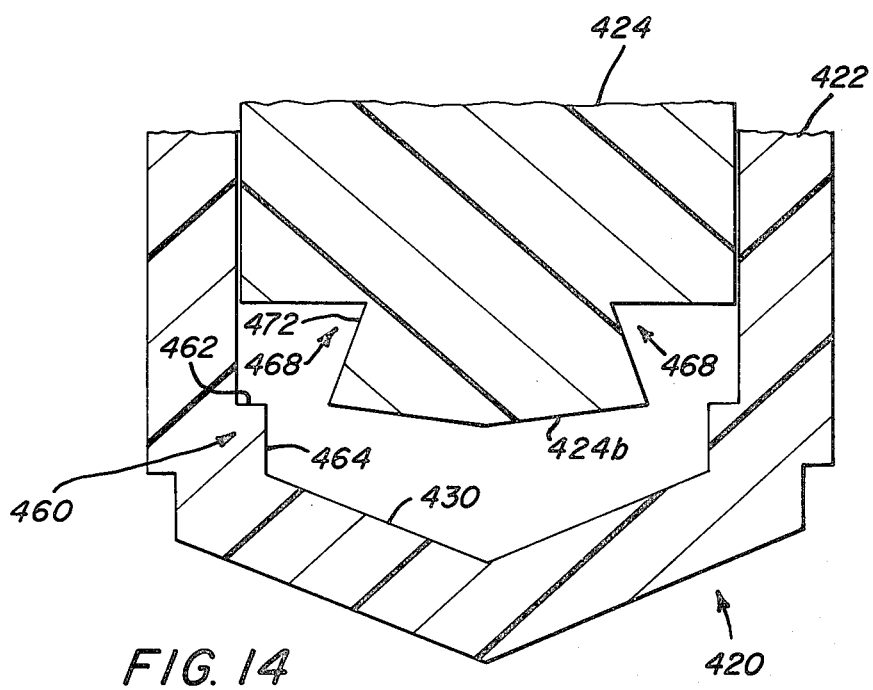
FIG. 14 is a view similar to FIG. 5A of still another embodiment of the present invention.

Considering now FIG. 14, another embodiment of applicant's invention is illustrated. This embodiment is similar to the embodiment illustrated in FIG. 13 and reference numerals in the "400" series will be used to identify components similar to components previously described.

FIG. 14 illustrates a clamping device 420 having a roller 424 movable with respect to a body member 422. The body member 422 has a V-shaped bottom wall or floor 430 shaped in a manner similar to the floor 30 of the embodiment illustrated in FIG. 5A. The outer peripheral portion 424b of the roller is shaped similar to the outer peripheral portion of the roller 24 in FIG. 5A. Also, the roller 424 has roller grooves 468 similar to the roller grooves 368 used with the embodiment illustrated in FIG. 13. As with the embodiment of FIG. 13, the maximum distance between the roller surface 472 and the side wall of the body member 422 is such that no flow lumens are formed in side portions of the tubing. The distance between the edge of the peripheral portion 424b and the ledge surface 464 is preferably approximately equal to the uncompressed nominal thickness of one wall of the tubing.

The embodiments illustrated in FIGS. 13 and 14 are designed to minimize the adverse effects of abusive tugs on compressed tubing. The roller grooves are cut so that the sides of the tubing tend to bulge into the spaces formed between the grooves and side walls of the body member. When the tubing is subjected to an abusive tug, the inclined surfaces tend to resist movement of the tubing so that the central region of the tubing maintains its desired configuration, and the flow rate is not changed. Another advantage provided by the tapered side walls of the roller is the tendency of tubing to self center with respect to the roller body during translation of the roller.

While FIGS. 13 and 14 illustrate grooves having planar walls, other surfaces are usable to define one or both of the groove walls. Whatever the shape selected, it is preferable for the compressive forces acting on the sides of the tubing to be greatest in the region adjacent edges of the roller outer peripheral portion. In this manner, any tendency of the tubing side walls to move inwardly when the tubing is subjected to an abusive tug is resisted. Also, the rollers illustrated in FIGS. 13 and 14 can be combined with a body member of the type illustrated in FIG. 8.

As in the previously described embodiments, when the apex angle of the roller is 60° or slightly more, the point or apex of the V-shape of the roller is slightly rounded or curved to facilitate movement of the roller along the tubing. Also, the V-shaped portion of the roller can be slightly knurled or axially slotted or ridged, as generally indicated in FIG. 1, to facilitate turning of the roller. Further, this provides a limited degree of frictional resistance between the compressed tubing and the roller that tends to maintain the roller in a desired position. In addition, the side walls of the roller adjacent the side walls of the body member can be serrated or formed with ridges to reduce the possibility of slippage between the sides of the roller and the side walls of the body member.

The invention has been described in detail with particular reference to preferred embodiments thereof, but it will be understood that variations and modifications can be effected within the spirit and scope of the invention. For instance, the embodiments of applicant's invention illustrated in FIGS. 1-8 and 13-14 can be combined with the embodiment illustrated in FIGS. 9-12 to form a device in which the slots for guiding the trunnions of the rollers are angled progressively downwardly in a direction toward the distal end of the body and the apex angle of the bottom wall increases in a direction toward the distal end of the body. In addition, the apex angle of the bottom wall in the embodiments illustrated in FIGS. 1-8 and 13-14 can be abruptly increased at the far distal end of the clamping device to equal the apex angle of the roller rather than being progressively increased as in the embodiment illustrated in FIGS. 9-12. These and other modifications of the disclosed devices will be readily apparent to those skilled in the art and are intended to be covered by the appended claims.

What is claimed is:

1. An intravenous tubing clamping device for controlling fluid flow through compressible tubing comprising:
    an elongated body member adapted to receive said tubing having a proximal end and a distal end;
    said body member including a generally V-shaped bottom wall defining two planar supporting surfaces for said tubing extending longitudinally of said body member and having a substantially constant width and an apex angle of about 60° to 165°; and
    a roller mounted on said body member for movement longitudinally of said body member about an axis of rotation extending transversely of said body member for defining a clamping area between said roller and said supporting surfaces which decreases the cross-sectional area of the lumen of the tubing as said roller moves from said proximal end of said body member toward said distal end, said roller defining grooves extending circumferentially around opposite sides of the outer circumference of said roller, said roller grooves defining spaces adapted to receive the sides of a tubing clamped in said clamping area, said roller grooves being defined by (1) side walls on said body member extending substantially parallel to said longitudinal roller movement on opposite sides of said roller, (2) first surfaces formed circumferentially on said roller adjacent to and on opposite sides of said clamping area, and (3) second surfaces formed circumferentially on said roller substantially perpendicular to said body member walls and each extending substantially parallel to said axis of rotation between a respective first surface and body member wall, said roller grooves cooperating with said body member to clamp the sides of said tubing in a direction transverse of said body member with said tubing being compressively engaged between said body member walls and said first surfaces, said first surfaces being inclined inwardly so as to form acute angles with said second surfaces thereby reducing the width of said roller in a region spaced inwardly from the outer circumference of the roller, the outer peripheral portion of said roller having distal ends merging with the portions of said roller defining said grooves, and said tubing being positively engaged by said second surfaces so that a lumen is defined in a central portion of the tubing through which flows substantially all of the fluid, said roller having a circumference with a generally V-shape with the apex of the V-shape centrally located on the roller and its distal ends merging with said roller grooves, the apex having an angle of about 60° to 180°, the roller cooperating with the planar supporting surfaces of said body member to define a generally V-shaped lumen in the clamped tubing.

2. An intravenous tubing clamping device according to claim 1, wherein said tubing is positively engaged by said second surfaces during movement of said roller towards the distal end of said body member.

3. An intravenous tubing clamping device as claimed in claim 1, wherein the apex angle of the bottom wall of the body member is progressively changed from a value less than the apex angle of the roller to a value approximately equal to the apex angle of the roller by moving the apex of the bottom wall in an upward direction.

4. An intravenous tubing clamping device as claimed in claim 1, wherein the apex angle of the roller is at least 10° more than the apex angle of the bottom wall.

5. An intravenous tubing clamping device as claimed in claim 1, wherein said roller has planar roller surfaces cooperating with said planar supporting surfaces of said body member to form a V-shaped lumen in a central portion of clamped tubing.

6. An intravenous tubing clamping device as claimed in claim 1, wherein the distance between the distal ends of said generally V-shaped bottom wall and the outer circumference of said roller adjacent said roller grooves measured along a line substantially perpendicular to said axis of rotation of said roller is about 1.6 to 2.2 times the uncompressed nominal wall thickness of said tubing when said tubing is clamped.

7. An intravenous tubing clamping device as claimed in claim 6, wherein said distance is about 1.8 times the uncompressed nominal wall thickness of said tubing.

8. An intravenous tubing clamping device as claimed in claim 1, wherein said roller has axially extending trunnions, and wherein said body member includes means for supporting said trunnions for movement toward the bottom wall as said roller moves from said proximal end of said body member toward said distal end.

9. An intravenous tubing clamping device as claimed in claim 1, wherein said device further comprises guide means on said body member for guiding longitudinal movement of said roller, the distance from the guide means to the bottom wall progressively decreasing toward the distal end of the body member.

10. An intravenous tubing clamping device as claimed in claim 9, wherein the apex angle of the V-shaped groove in the bottom wall increases over at least a portion of the length of the V-shaped groove in a direction from the proximal to the distal end of the body member.

11. An intravenous tubing clamping device as claimed in claim 1, wherein the apex angle of the V-shaped groove in the bottom wall increases over at least a portion of the length of the V-shaped groove in a direction from the proximal to the distal end of the body member.

12. An intravenous tubing clamping device for controlling fluid flow through compressible tubing comprising:
an elongated body member adapted to receive said tubing having a proximal end and a distal end;
said body member including a generally V-shaped bottom wall defining two planar supporting surfaces for said tubing extending longitudinally of said body member and having a substantially constant width and an apex angle of about 60° to 165°, said body member further including grooves extending longitudinally on opposite sides of said V-shaped bottom wall, outer edges of said planar supporting surfaces defining top edges of said body member grooves, said body member grooves defining spaces adapted to receive a portion of the sides of a clamped tubing; and
a roller mounted on said body member for movement longitudinally of said body member about an axis of rotation extending transversely of said body member for defining a clamping area between said roller and said planar supporting surfaces which decreases the cross-sectional area of a lumen formed in a central region of the clamped tubing as said roller moves from said proximal end of said body member toward said distal end, said roller defining grooves extending circumferentially around opposite sides of the outer circumference of said roller, said roller grooves defining spaces adapted to receive a portion of the sides of a tubing clamped in said clamping area, said roller grooves being shaped so that the clamping forces on the sides of the tubing are greatest in the vicinity of the edges of the outer peripheral portion of said roller and decrease in a direction extending towards the axis of rotation.

13. An intravenous tubing clamping device as claimed in claim 12, wherein the depth of said roller grooves and said body member grooves is approximately equal to the uncompressed nominal wall thickness of said tubing.

14. An intravenous tubing clamping device as claimed in claim 12, wherein said body member grooves and said roller grooves clamp sides of the tubing so that no flow lumens are formed at sides of the tubing.

15. An intravenous tubing clamping device as claimed in claim 12, wherein the width of said roller grooves and said body member grooves is less than about 2 times the uncompressed nominal wall thickness of said tubing.

16. An intravenous tubing clamping device as claimed in claim 12, wherein said width of said roller grooves and said body member grooves is about 1.2 to 1.5 times the uncompressed nominal wall thickness of said tubing.

17. An intravenous tubing clamping device as claimed in claim 12, wherein the width of said body member grooves is greater than the width of said roller grooves.

18. An intravenous tubing clamping device as claimed in claim 12, wherein the depth of said body member grooves and the depth of said roller grooves are approximately the same.

19. An intravenous tubing clamping device as claimed in claim 12, wherein said body member grooves and said roller grooves compress both sides of the tubing in a direction substantially parallel to an axis of the roller to thereby minimize a change in flow rate when the tubing is subjected to an abusive tug.

20. An intravenous tubing clamping device as claimed in claim 12, wherein the widths of said body member grooves and said roller grooves are less than twice the width of uncompressed tubing so that sides of said tubing are clamped in a direction transverse of said body member to thereby oppose movement of the tubing when the tubing is subjected to an abusive tug.

21. An intravenous tubing clamping device as claimed in claim 12, wherein said roller grooves are defined by first surfaces extending inwardly from opposite sides of the outer peripheral portion of the roller and second surfaces extending from inner edges of said first surfaces towards side walls of said body member, said roller having a central portion with outer edges merging with outer edges of said second surfaces, extensions of said first surfaces forming acute angles with the axis of rotation.

22. An intravenous tubing clamping device according to claim 21, wherein said second surfaces extend generally parallel to the axis of rotation.

23. An intravenous tubing clamping device according to claim 12, wherein the width of said roller is decreased by the grooves so that the distance between sides of the roller and side walls of said body member increases in a direction extending from the outer peripheral portion towards the axis of rotation of the roller, the roller having a central portion with a width greater than the width of the outer peripheral portion.

* * * * *